US00PP21635P2

(12) United States Plant Patent
Meinl

(10) Patent No.: US PP21,635 P2
(45) Date of Patent: Jan. 18, 2011

(54) ***HYDRANGEA* PLANT NAMED 'HORORB'**
(50) Latin Name: *Hydrangea macrophylla*
Varietal Denomination: HorOrb

(75) Inventor: Katrin Meinl, Dresden (DE)

(73) Assignee: Claus + Tosken Kühne GbR, Dresden (DE)

( * ) Notice: Subject to any disclaimer, the term of this patent is extended or adjusted under 35 U.S.C. 154(b) by 0 days.

(21) Appl. No.: 12/653,201

(22) Filed: Dec. 9, 2009

(51) Int. Cl.
*A01H 5/00* (2006.01)

(52) U.S. Cl. ..... Plt./250
(58) Field of Classification Search ..... Plt./250

See application file for complete search history.

*Primary Examiner*—Annette H Para
(74) *Attorney, Agent, or Firm*—C. A. Whealy

(57) ABSTRACT

A new and distinct cultivar of *Hydrangea* plant named 'HorOrb', characterized by its upright and mounded plant habit; black-colored stems; strong and dark green-colored leaves; and mophead-type inflorescences with dark pink-colored flowers.

3 Drawing Sheets

Botanical designation: *Hydrangea macrophylla.*
Cultivar denomination: 'HORORB'.

BACKGROUND OF THE INVENTION

The present invention relates to a new and distinct cultivar of *Hydrangea* plant, botanically known as *Hydrangea macrophylla* and hereinafter referred to by the name 'HorOrb'.

The new *Hydrangea* plant is a naturally-occurring branch mutation of a proprietary selection of *Hydrangea macrophylla* identified as code number 10-9915, not patented. The new *Hydrangea* plant was discovered and selected in 2003 from a single plant within a population of plants of the parent selection in a controlled greenhouse environment in Dresden, Germany.

Asexual reproduction of the new cultivar by softwood cuttings in Dresden, Germany since 2003 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'HorOrb'. These characteristics in combination distinguish 'HorOrb' as a new and distinct cultivar of *Hydrangea:*

1. Upright and mounded plant habit.
2. Black-colored stems.
3. Strong and dark green-colored leaves.
4. Mophead-type inflorescences with dark pink-colored flowers.

Plants of the new *Hydrangea* differ primarily from plants of the parent selection in the following characteristics:

1. Plants of the new *Hydrangea* have longer internodes than plants of the parent selection.

2. Plants of the new *Hydrangea* have black-colored stems whereas plants of the parent selection have green-colored stems.

Plants of the new *Hydrangea* can be compared to plants of *Hydrangea* 'Nigra', not patented. Plants of the new *Hydrangea* differ primarily from plants of 'Nigra' in the following characteristics:

1. Plants of the new *Hydrangea* have thicker stems than plants of 'Nigra'.
2. Plants of the new *Hydrangea* have larger inflorescences than plants of 'Nigra'.
3. Flowers of plants of the new *Hydrangea* have larger sepals than flowers of plants of 'Nigra'.

BRIEF DESCRIPTION OF THE PHOTOGRAPHS

The accompanying colored photographs illustrate the unique appearance of the new *Hydrangea* plant, showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a close-up view of a typical flowering plant of 'HorOrb' grown in a container.

The photograph on the second sheet is a close-up view of developing inflorescences of 'HorOrb'.

The photograph on the third sheet is a close-up view of a typical fully developed lateral branch and inflorescence of 'HorOrb'.

DETAILED BOTANICAL DESCRIPTION

Plants used in the aforementioned photographs and in the following description were grown during the summer and autumn in Grand Haven, Mich. in an outdoor nursery and under conditions which closely approximate commercial production conditions. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea macrophylla* 'HorOrb'.

Parentage: Naturally-occurring branch mutation of a proprietary selection of *Hydrangea macrophylla* identified as code number 10-9915, not patented.

Propagation:

*Type cutting.*—By softwood cuttings.

*Time to initiate roots.*—About 18 days at temperatures of about 24° C.

*Time to produce a rooted young plant.*—About two months at temperatures of about 24° C.

*Root description.*—Fine to thick; creamy white in color.

*Rooting habit.*—Freely branching; dense.

Plant description:

*Form/growth habit.*—Perennial shrub; upright and mounded plant habit; broadly inverted triangle; freely branching habit, about twelve lateral branches develop per plant; strong lateral branches; vigorous growth habit.

*Plant height.*—About 80 cm.

*Plant diameter or area of spread.*—About 50 cm.

*Lateral branches.*—Length: About 60 cm. Diameter: About 6 mm. Internode length: About 11 cm. Texture: Smooth, glabrous; woody with development. Strength: Strong. Color: Close to 202A; woody stems, close to 165A.

Foliage description:

*Arrangement.*—Opposite, simple.

*Length.*—About 17 cm.

*Width.*—About 9 cm.

*Shape.*—Ovate.

*Apex.*—Acute.

*Base.*—Cuneate.

*Margin.*—Serrate.

*Texture, upper and lower surfaces.*—Smooth, glabrous; rugose.

*Venation pattern.*—Pinnate.

*Color.*—Developing leaves, upper surface: Close to 141A. Developing leaves, lower surface: Close to 141C. Fully developed leaves, upper surface: Close to 131A; venation, close to 141C. Fully developed leaves, lower surface: Close to 141A; venation, close to 141C.

*Petiole.*—Length: About 3 cm. Diameter: About 5 mm. Texture, upper and lower surfaces: Smooth, glabrous. Color, upper surface: Close to 141C. Color, lower surface: Close to 202A.

Flower description:

*Flower type and habit.*—Single sterile and fertile flowers arranged on terminal mophead-type panicles; fertile and sterile flowers face upright to outwardly.

*Fragrance.*—None detected.

*Natural flowering season.*—Continuous flowering from June to October in Grand Haven, Mich.; early flowering habit, plants begin flowering about 13 weeks after planting.

*Flower longevity, fertile flowers.*—Flowers last about one week on the plant; flowers not persistent.

*Flower longevity, sterile flowers.*—Flowers last about four months on the plant; flowers persistent.

*Quantity of flowers.*—Freely flowering; about six flowers and about 63 sterile flowers per panicle.

*Panicle height.*—About 15 cm.

*Panicle diameter.*—About 20 cm.

*Flower diameter, fertile flowers.*—About 7 mm.

*Flower depth (height), fertile flowers.*—About 5 mm.

*Flower diameter, sterile flowers.*—About 9 cm.

*Flower depth (height), sterile flowers.*—About 4 cm.

*Flower buds, fertile and sterile flowers.*—Length: About 6 mm. Diameter: About 4 mm. Shape: Obovate. Color: Close to 145B.

*Petals, fertile flowers only.*—Quantity/arrangement: Four in a single whorl. Length: About 4 mm. Width: About 3 mm. Shape: Elliptic. Apex: Acute. Base: Attenuate. Margin: Entire. Texture, upper and lower surfaces: Smooth, glabrous. Color: When opening, upper surface: Close to 66B. When opening, lower surface: Close to 66D. Fully opened, upper surface: Close to 66C. Fully opened, lower surface: Close to 66D.

*Sepals, fertile flowers.*—Quantity/arrangement: Four in a single whorl. Length: About 1 mm. Width: About 0.5 mm. Shape: Rounded lobe. Apex: Obtuse. Base: Fused. Margin: Entire. Texture, upper and lower surfaces: Smooth, glabrous. Color, upper and lower surfaces: Close to 145B.

*Sepals, sterile flowers.*—Quantity/arrangement: Four in a single whorl. Length: About 4.2 cm. Width: About 5 cm. Shape: Nearly reniform. Apex: Obtuse to retuse. Base: Obtuse to truncate. Margin: Entire. Texture, upper and lower surfaces: Smooth, glabrous. Color: When opening, upper and lower surfaces: Close to 145B. Fully opened, upper surface: Close to 67A to 67B. Fully opened, lower surface: Close to 68B.

*Peduncles, fertile and sterile flowers.*—Angle: Erect to about 20° from vertical. Strength: Strong. Length: About 8 cm. Diameter: About 5 mm. Texture: Smooth, glabrous. Color: Close to 202A.

*Pedicels, fertile flowers.*—Angle: Erect to about 30° from vertical. Strength: Moderately strong. Length: About 4 mm. Diameter: About 1 mm. Texture: Smooth, glabrous. Color: Close to 67A.

*Pedicels, sterile flowers.*—Angle: Erect to about 45° from vertical. Strength: Strong. Length: About 3 cm. Diameter: About 2 mm. Texture: Smooth, glabrous. Color: Close to 67A.

*Reproductive organs, fertile flowers only.*—Stamens: Quantity per flower: About five. Anther length: About 1 mm. Anther shape: Oblong. Anther color: Close to 202C. Pollen amount: Scarce. Pollen color: Close to 202C. Pistils: Pistil quantity per flower: One. Pistil length: About 1 mm. Stigma shape: Globular. Stigma color: Close to 67C. Style length: About 1.5 mm. Style color: Close to 87C. Ovary color: Close to 145B.

*Seeds/fruits.*—Seed and fruit development have not been observed on plants of the new *Hydrangea*.

Disease/pest resistance: Plants of the new *Hydrangea* have not been observed to be resistant to pathogens and pests common to *Hydrangea*.

Temperature tolerance: Plants of the new *Hydrangea* have been shown to be tolerant to temperatures ranging from about −25° C. to about 38° C.

It is claimed:

1. A new and distinct *Hydrangea* plant named 'HorOrb' as illustrated and described.

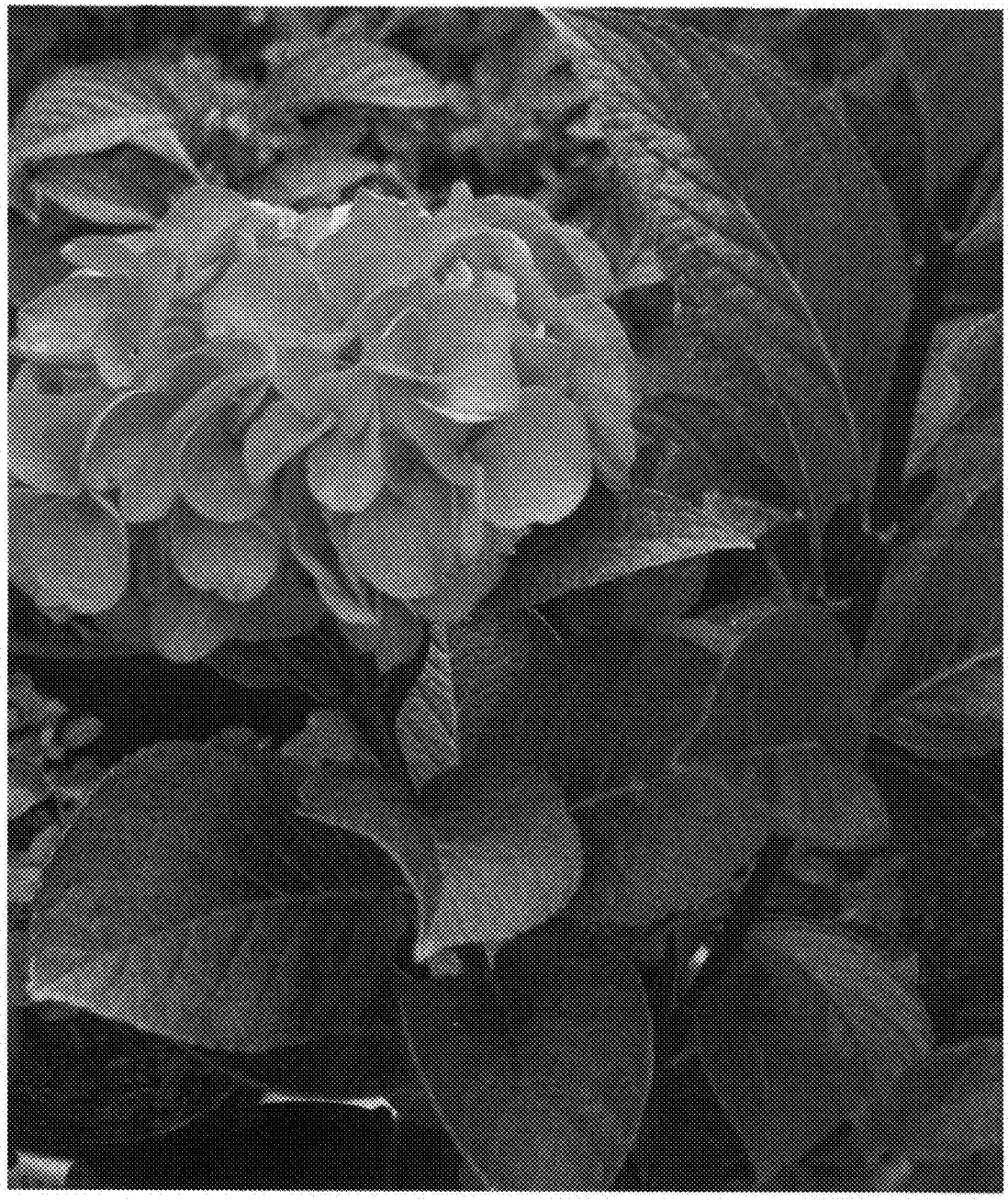

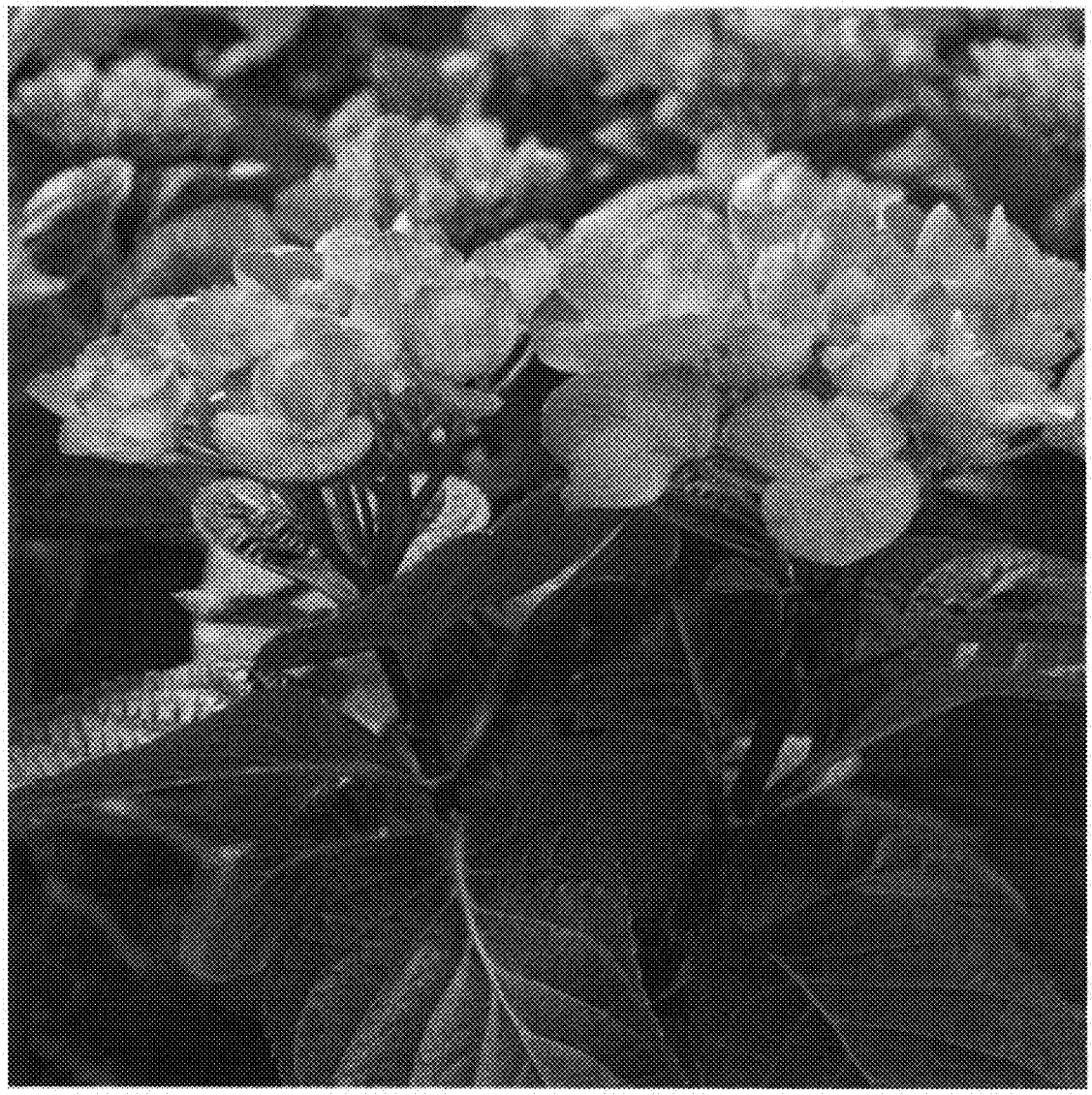

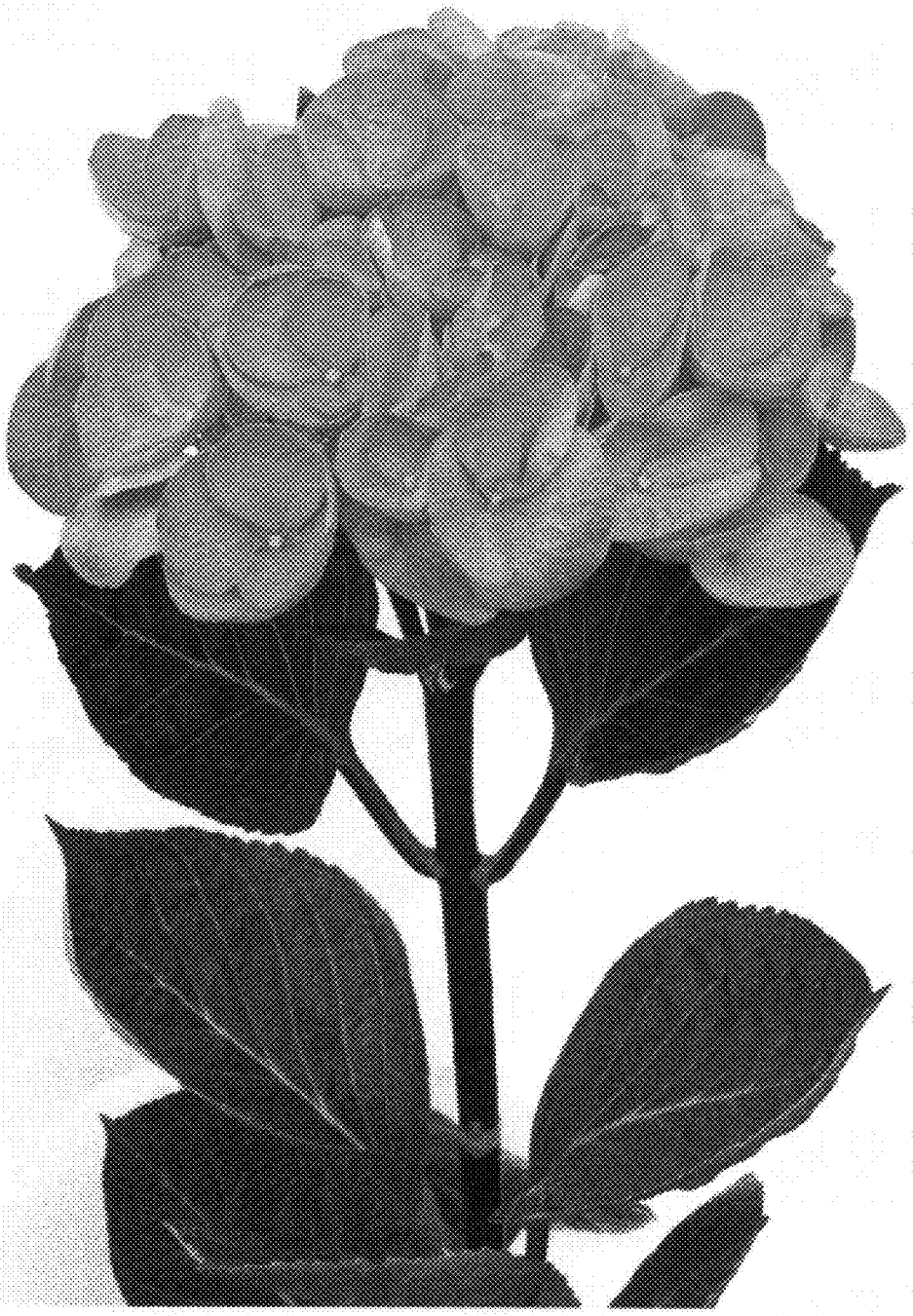

* * * * *